United States Patent [19]

Landefeld et al.

[11] Patent Number: 4,474,050

[45] Date of Patent: Oct. 2, 1984

[54] FOUNDRY COKE TEST APPARATUS

[75] Inventors: Craig F. Landefeld, Troy; Seymour Katz, Huntington Woods, both of Mich.

[73] Assignee: General Motors Corporation, Detroit, Mich.

[21] Appl. No.: 482,956

[22] Filed: Apr. 7, 1983

[51] Int. Cl.³ .......................... G01N 3/00; G01N 15/08
[52] U.S. Cl. ............................................ 73/12; 73/38; 73/432 PS
[58] Field of Search ........................ 73/12, 38, 432 PS

[56] References Cited

U.S. PATENT DOCUMENTS 2,733,595  2/1956  Twining ................................... 73/38
3,608,357  9/1971  Meunier ................................... 73/38

Primary Examiner—S. Clement Swisher
Attorney, Agent, or Firm—George A. Grove

[57] ABSTRACT

A testing apparatus for measuring gas flow through a test sample bed of foundry cupola coke incidental to determining the hydraulic radius of the sample, the apparatus comprising a hollow cylindrical walled container where the internal wall has an elastomeric foam layer that is penetrated by the adjacent coke particles to minimize wall effects due to high porosity at the wall. In an optional feature, the coke may be introduced into the bed through a shatter tower that simulates breakup of the coke in an operating cupola.

3 Claims, 3 Drawing Figures

FOUNDRY COKE TEST APPARATUS

This invention relates to the measurement of the effectiveness of foundry coke in a cupola melting furnace. More particularly, this invention relates to a practical foundry testing apparatus for predicting the performance of a batch of foundry coke in a cupola furnace.

Cupola melting is used to convert iron, and/or steel scrap to liquid cast iron. A cupola furnace typically comprises a tall, vertical, water-cooled, hollow steel shaft. At the bottom of the shaft is a sloping refractory hearth on which the molten iron collects. A tap hole in the shaft at hearth level is provided to drain molten iron. Toward the bottom of the shaft above the hearth are a plurality of tuyeres located circumferentially about the shaft for blowing combustion air into it. In the operation of the cupola alternate charges of coke (fuel), iron and steel, and limestone are added near the top of the shaft. Metal melts some distance above the tuyeres leaving a bed of incandescent coke below that level.

Coke plays a very important role in the melting process. It supplies most of the energy required for melting and super-heating the iron. It also affects the carbon content of the liquid iron composition. Air blown into the cupola reacts quickly with the coke in a highly exothermic reaction to form carbon dioxide. The rising carbon dioxide gas further reacts with coke to form carbon monoxide. This reaction consumes coke and is endothermic. Therefore, forming carbon monoxide is largely detrimental in melting iron. Accordingly, a key to reducing the percentage of coke needed in the cupola charge is to reduce the rate of carbon monoxide formation in the coke bed.

One of us, Katz, has shown that over most of the temperature range in which carbon monoxide forms at an appreciable rate, the rate of carbon monoxide formation is limited by the rate of mass transfer of carbon dioxide and carbon monoxide between the gas phase in the cupola and the external surfaces of the coke lumps. It was further shown that the mass transfer rate is inversely proportional to the ratio of interparticle void volume to the external surface area of the coke. This ratio of bed porosity to surface area is called the hydraulic radius, $R_h$, of the bed. Thus, the hydraulic radius of a bed formed by a sample of coke is an important measure of the utility of that lot of coke in a cupola melting furnace.

The hydraulic radius of a coke bed can be determined from the pressure drop through a bed of known height and porosity through which gas of known density, temperature, pressure and viscosity is flowing at a known rate.

Hydraulic radius, $R_h$, can be expressed as $$R_h = \frac{E\, D_{eq}}{6(1-E)} \quad [1]$$

1. R. B. Bird et al, Transport Phenomena (Wiley, N.Y., 1960), pp 196–197.

where E is fraction of void volume in the coke bed and $D_{eq}$ is the diameter of a sphere having the same surface area-to-volume ratio as the bed of coke lumps. $D_{eq}$ is determined using the well-known Ergun equation $$\frac{\Delta P}{L} \frac{P_g D_{eq}}{G^2} \frac{E^3}{1-E} = \frac{A(1-E)}{G D_{eq}/u} + B \quad [2]$$

2. S. Ergun, "Fluid Flow through Packed Columns," Chemical Engineering Progress, Vol. 48, No. 2 (1952), pp 89–94.

in which $\Delta P$ is the pressure drop, L is bed height, $P_g$ is gas density, G is mass flux, and u is gas viscosity.

A & B are experimental constants dependent on the nature of the bed packing.

We determined A and B from a linear plot $$\frac{\Delta P}{L} \frac{P_g D_{eq}}{G^2} \frac{E^3}{1-E} \text{ as a function of } \frac{(1-E)u}{G\, D_{eq}}.$$

Before this is done, two characteristics of the coke sample must be determined in order to evaluate $D_{eq}$. Its size distribution must be determined; we did this by screening (sieving). Also, a shape factor must be determined, which relates surface area-to-volume ratio of a coke lump to a linear measure of its size, such as the screen opening. We determined the shape factor by a sectioning method. The shape factor is a characteristic of the type of particle, and need be determined only once.

After thus determining the constants A and B, we solved the Ergun equation for $D_{eq}$, then replaced $D_{eq}$ with $6(1-E)R_h/E$, and after rearranging obtained the following relation expressing $R_h$ as a function of measured variables:

$$R_h = \frac{E}{6(1-E)}\left[\frac{B + \sqrt{B^2 - 4ac}}{2a}\right]$$

where $$a = \frac{\Delta P}{L} \frac{P_g}{G^2} \frac{E^3}{1-E}$$

and $$c = -A(1-E)\, u/G$$

It is, of course, impractical to measure the hydraulic radius in the bed of an operating cupola. It is also awkward to provide a test container for foundry coke because the coke is quite large, up to 22 centimeters in diameter. In order to make accurate and repeatable fluid flow measurements through a bed of coke lumps of this size, according to conventional practice, a container would have to be 2 to 4 meters in diameter to minimize the effect of the coke particles orienting themselves at the wall of the container and producing a greater bed porosity, E, than in the bulk. This effect is known as a wall effect and is quite significant in fluid flow measurements through a porous bed if an appropriately-sized container is not used.

Accordingly, it is an object of our invention to provide a practically-sized, effective hydraulic radius test apparatus for evaluating foundry coke. It is a further object of our invention to provide such a test apparatus which also subjects the coke to breaking or fracturing stresses such as the coke encounters in an operating cupola.

BRIEF SUMMARY OF THE INVENTION

In accordance with a preferred embodiment of our invention, these and other objects and advantages are accomplished as follows An open-ended, hollow, cylindrical, walled container is provided. It is vertically oriented. An important aspect of the container is that the inside wall is lined with a compliant material such as polyurethane foam. When a test sample bed of coke is formed in the container the corners, or asperities, of the pieces of coke penetrate into the compliant wall lining. This penetration markedly reduces the porosity at the wall to a level more like the bulk of the bed. This feature permits us to obtain useful fluid flow data with a smaller container and more manageable sample.

Affixed at the bottom of the container is a grate which has openings suitable to support a test bed of coke and admit a gas stream. A conduit means is also connected to the bottom of the coke bed container to supply a flow of gas at a known pressure and flow rate for purposes of determining the hydraulic radius of the test coke bed. Means are also provided to measure the volume and weight of the bed.

An optional feature of our invention is the provision of a shatter tower above the upper open end of our container. Coke admitted to the test bed container is dropped down the shatter tower to simulate the breakage experienced by the coke in an operating cupola. The shatter tower is characterized by a number of parallel vertical conduit sections arranged end-to-end but slightly offset from each other. Each has an inclined impact plate at its bottom end. For example, with a three section tower, a piece of coke falling down the first section, strikes the inclined impact plate and is knocked laterally into the second section. There it drops until it strikes the next impact plate and rebounds into the third section where it drops to the bottom of the tower. It tumbles from the last impact plate and drops into the test bed container. Pieces may be fractured off the coke in this shatter tower just as the coke may be fractured in an operating cupola.

Once a test bed of coke particles is thus built up in our compliant wall container, a test gas (such as air) may be passed upwardly through the coke bed for the purpose of determining the hydraulic radius of the pieces in the bed. This practice will be discussed further as we describe in more detail our test apparatus.

SUMMARY OF THE DRAWINGS

Further advantages of our invention will be understood following a detailed description thereof in which reference will be made to the drawings.

DETAILED DESCRIPTION OF THE PREFERRED EMBODIMENT

Figure 1:
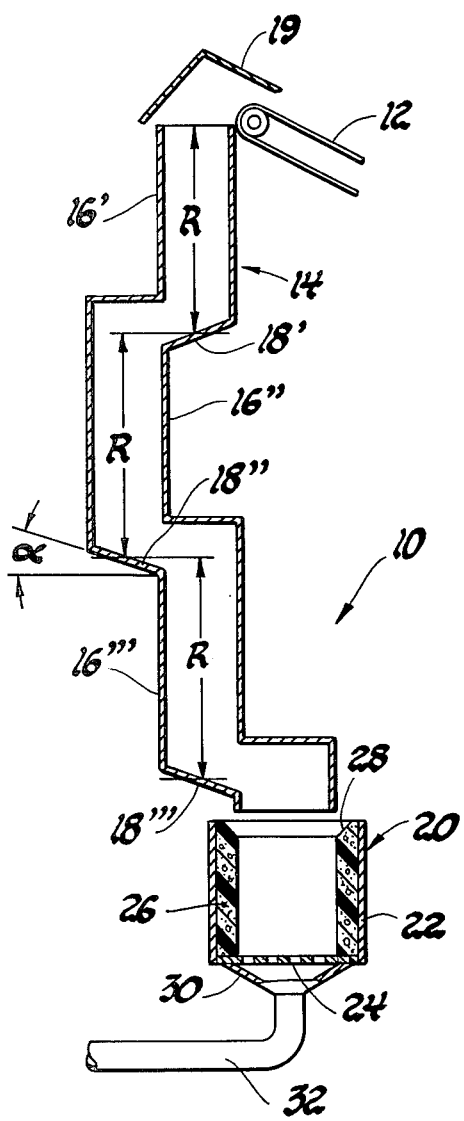
FIG. 1 is a sectional elevation of our coke testing apparatus.

Our test apparatus 10 is depicted in cross-section in FIG. 1. We will describe the apparatus as it would be used with the introduction of coke into the apparatus and followed by the testing of the coke.

A conveyor belt 12 is provided, for carrying coke to the top of shatter tower 14. Shatter tower 14 comprises three hollow vertical conduit sections 16', 16" and 16'''. Coke entering the top of the upper-most section 16' falls a distance R onto a steel impact plate 18'. Steel plate 18' is inclined at an angle, alpha ($\alpha$), from the horizontal plane. The distance R depends on the incline, alpha, which will be explained in more detail below. Coke striking impact plate 18' rolls or bounces into the adjacent lower and offset tower section 16" where it again falls a like distance (R) and receives a like impact on plate 18". The coke falls a third time in the third section 16''' of the shatter tower (a distance R) until it strikes a third impact plate 18''' from which it bounces or drops into the hydraulic radius tester container 20. The tower 14 may have a cover 19.

The hollow cylindrical hydraulic radius tester container 20 has a circular steel wall 22. Container 20 has a grate 24 at its lower end. Grate 24 supports the coke bed (not shown in FIG. 1) and is perforated to allow for gas to be admitted up into the container. The tester vessel has a compliant internal wall lining 26 of suitable thickness and flexibility to be penetrated by the coke (not shown in FIG. 1) and reduce the high porosity that normally exists in a coke bed at a rigid container wall. This is a key feature of our apparatus and will be discussed further below. The height of the coke bed may be measured by any suitable means such as graduations on the internal surface of the container wall (not shown) or by striking off level with the top. The upper opening of the container suitably has a conical inlet section 28 to direct coke from the shatter tower 14 into the vessel.

It is desired to be able to introduce gas to the bottom of the coke bed such that the gas velocity is the same over the entire grate area. A conical diffuser 30 is provided at the inlet of the tester for this purpose. The same effect could be produced by substituting a bed of particles for the conical diffuser The hydraulic radius measuring container is connected to a flow gas source (not shown) through a conduit 32. The nature of the gas is arbitrary, however, the most convenient gas is air. The gas source, suitably an air blower, is connected to conduit 32. The volumetric gas flow rate in the conduit is determined by measuring the pressure drop across a known device such as a laminar flow element, an orifice plate or a venturi flow meter. Pressure in the conduit may be measured below the grate by an inclined manometer or an electronic pressure transducer. The temperature of the ambient gas is measured by a thermometer or thermocouple. A scale is used to measure the weight of the test unit 20 before and after it is filled with coke.

The equation expressed above may be used to obtain the hydraulic radius from values measured using the subject test apparatus. Mass flow rate, G, is calculated from the volumetric flow rate measured in conduit 32, the average of the gas (air) pressure below the bed in container 20 and of atmospheric pressure, the temperature of the gas, and the molecular weight of the gas. Gas density, $p_g$, is calculated from its molecular weight, temperature and pressure. The pressure drop is that measured between the bottom and top of the coke bed where the pressure at the top of the coke bed is ambient, atmospheric pressure. Bed length, L, is measured. Gas viscosity can be calculated knowing the identity and temperature of the gas. Bed porosity, E, is $1 - p_b/p_a$, where $p_b$ is the bulk density of the coke bed and $p_a$ is the average apparent density of an individual lump. The bulk density is equal to the weight of the coke in the tester divided by the volume of the tester. The apparent average density of a lump of coke is determined using standard methods.

It is widely recognized that foundry coke breaks up in the cupola as it works its way down the cupola shaft.

The breakage decreases the hydraulic radius of the bed actually formed by the coke. ASTM Drop Shatter Test, D141, seeks to reproduce the stresses imposed on coke in a reasonably representative cupola system by dropping a sample of coke four times a distance of 1.83 meters (6 feet) onto a steel plate. Our tower section with three or four impact points is designed to simulate these impacts. In our design, because of the incline of the steel plate, the drop distance needed to obtain a velocity normal to the plate that is the same obtained in the ASTM Test is a function of alpha. That relationship is:

$$R \text{ (meters)} = \frac{1.83}{\cos^2\alpha}$$

For alpha equals 30° the height must be 2.44 meters (8 feet).

The cross section of our shatter tower was a square of 0.41 meters on a side. The size was chosen large enough to avoid two lumps wedging and sticking in the tower. However, it is preferable that only one lump at a time strike the impact plate, in order to maximize the severity of impact.

Figure 2:
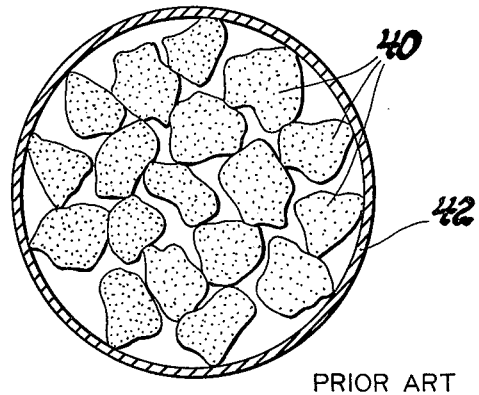
FIG. 2 is a sectional view of a test bed container illustrating the high wall porosity in a prior art rigid wall container.
Figure 3:
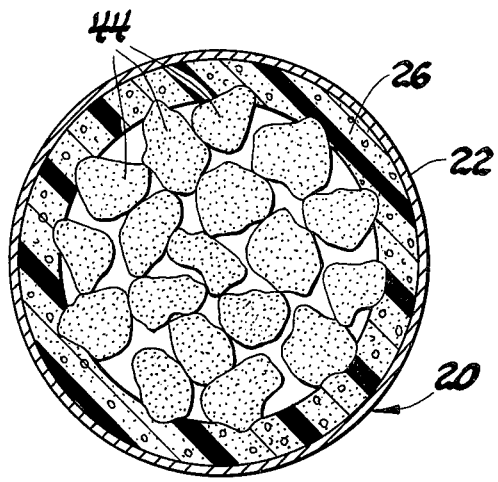
FIG. 3 is a sectional view illustrating the lower wall porosity with our compliant wall test bed container.

We now discuss the utility of our hydraulic radius tester container having the compliant interior wall surface. It is well established that to make accurate measurements of fluid flow through a particle bed, the diameter of the container should be at least twenty times the diameter of the particles. Since the nominal diameter of foundry coke is 0.1–0.2 meters, this would require the container to be two to four meters in diameter. This is normally impractical for useful foundry test purposes. Since the requirement for large diameter containers arises from the need to make wall porosity effects insignificant, we conceived the use of a compliant wall to greatly reduce this wall effect. The wall effect occurs because coke particles orientate themselves at a wall, producing a different configuration than in the bulk. Inside the outer layer of particles the orientation is progressively reduced. The wall orientation effect produces a very porous region at the wall surface through which an abnormally-high proportion of the gas will flow. FIG. 2 illustrates the excessive bed porosity of coke particles 40 at a rigid steel container wall 42. This is known in the prior art. As a result, the porosity is much higher at the wall and not representative of the porosity of the bulk. FIG. 3 is a cross sectional view of our container 20. The compliant wall 26 is seen to eliminate the abnormal porosity region adjacent the wall surface. The coke particles 44 penetrate the elastomeric wall liner 26 and the open volume is reduced. We have found that effect of compliant walls on hydraulic radius determinations on coke in relatively small containers is dramatic. Based on our experiments a hydraulic radius container having a diameter of only 0.81 meters (2.67 feet) is suitable for testing foundry coke.

We have formed our compliant wall out of a layer of polyurethane foam. We have found that it is suitable to use a layer of foam whose thickness is about half the nominal maximum diameter of the coke to be tested. We have used foams having densities of 64 kilograms per cubic meter, 32 kilograms per cubic meter, and 22 kilograms per cubic meter. We have found that differences in hydraulic radius data with differences in the choice of foam were relatively small. We generally prefer the least dense foam. Urethane foam is durable and preferred for our purposes. However, it will be appreciated that other durable and flexible elastomeric foams could be used.

We have used a circular cylindrical container. Other shapes (e.g. square) may be used.

Thus, we have provided a novel hydraulic radius tester that is particularly useful for foundry coke. By providing a cylindrical tester container with elastomeric foam compliant walls, we are able to satisfactorily obtain meaningful hydraulic radius data in a tester much smaller and more practical than could otherwise be obtained. In an optional feature of our invention, we can subject the coke samples to be tested to a shatter test equivalent to that conducted by ASTM Test D141 which produces a size distribution nearer that in an actual cupola bed. It will also be appreciated that our test device could be used to measure hydraulic radius on blast furnace coke and on materials other than coke.

Thus, while our invention has been described in terms of a specific embodiment for a specific application, it would be appreciated that our invention could be adapted by those skilled in the art to other forms. Accordingly, the scope of our invention is intended to be limited only by the scope of the following claims.

The embodiments of the invention in which an exclusive property or privilege is claimed are defined as follows:

1. A testing apparatus for measuring gas flow through a test bed of particles for determining the hydraulic radius of the particles, the apparatus comprising a hollow-open-mouthed wall container and a perforate closure member at one end adapted to support the bed of particles while admitting gas for the flow test, the inner wall being covered with a layer of relatively soft, compliant material adapted to be penetrated by particles to reduce the porosity of a test bed at said wall.

2. A testing apparatus for measuring gas flow through a test sample bed of coke for determining the hydraulic radius of the sample, the apparatus comprising a hollow-open-mouthed wall container and a perforate closure member at one end adapted to support the bed of coke while admitting gas for the flow test, the inner wall being covered with a layer of relatively soft, compliant material adapted to be penetrated by adjacent coke particles to reduce the porosity of a test sample bed at said wall.

3. A testing apparatus for evaluating a sample bed of foundry coke for use in a cupola furnace, comprising,
   a vertically disposed, hollow, walled container having a perforate closure at the lower end adapted to support a test sample bed of coke while admitting a gas up through the test bed, an opening at the upper end adapted to admit said coke and to exhaust said gas, and a compliant foam lining layer on the internal surface of the wall adapted to be penetrated by the coke pieces adjacent the wall to reduce porosity at the wall, and
   a vertical tower over the container and adapted for coke pieces to be dropped through the tower and subjected to several impacts before falling into said container, said tower comprising a plurality of open ended vertical sections each having an inclined impact plate at its bottom end, the sections being arranged vertically end-to-end with the upper end of a lower section being offset laterally from the lower end of the adjacent upper section such that a piece of coke falling down a tower section strikes an impact plate at the bottom and is thereby deflected sideways into the next lower section or into the container, the apparatus thus being adapted to first subject an added sample of coke pieces to impact forces like those encountered in a cupola furnace and then to permit the measurement of fluid flow through a contained bed of coke pieces with minimal container wall effects on such flow.

* * * * *